United States Patent
Baschong et al.

(10) Patent No.: US 7,425,320 B2
(45) Date of Patent: Sep. 16, 2008

(54) USE OF GUAIOL FOR TREATING THE SKIN

(75) Inventors: Werner Baschong, Basel (CH); Gerd Heinemann, Schliengen (DE); Dietmar Ochs, Schopfheim (DE)

(73) Assignee: Ciba Specialty Chemicals Corp, Tarrytown, NY (US)

( * ) Notice: Subject to any disclaimer, the term of this patent is extended or adjusted under 35 U.S.C. 154(b) by 434 days.

(21) Appl. No.: 10/489,645

(22) PCT Filed: Sep. 10, 2002

(86) PCT No.: PCT/EP02/10163

§ 371 (c)(1),
(2), (4) Date: Sep. 20, 2004

(87) PCT Pub. No.: WO03/024417

PCT Pub. Date: Mar. 27, 2003

(65) Prior Publication Data

US 2005/0058610 A1    Mar. 17, 2005

(30) Foreign Application Priority Data

Sep. 18, 2001  (EP)  ................... 01810902

(51) Int. Cl.
*A61Q 19/02* (2006.01)
*A61Q 17/00* (2006.01)
*A61Q 19/00* (2006.01)
*A61Q 19/04* (2006.01)
*A61K 8/02* (2006.01)

(52) U.S. Cl. ............................ 424/62; 424/59; 424/60; 424/400; 424/401

(58) Field of Classification Search ................... 424/59, 424/60, 62, 400, 401
See application file for complete search history.

(56) References Cited

U.S. PATENT DOCUMENTS

2001/0019717 A1    9/2001    Nojiri et al. ................. 424/401

FOREIGN PATENT DOCUMENTS

| EP | 0 275 719 | 7/1988 |
| EP | 0 431 755 | 6/1991 |
| EP | 0 433 086 | 6/1991 |
| WO | 01/53441 | 7/2001 |

OTHER PUBLICATIONS

Joyce Teng Ee Lim et al., "Treatment of Melasma Using Kojic Acid in a Gel Containing Hydroquinone and Glycolic Acid", Dermatol. Surg., vol. 25, No. 4, pp. 282-284 (Apr. 1999).
Patent Abstracts of Japan Publication No. 10036247 (1996).

*Primary Examiner*—Shelley A. Dodson
(74) *Attorney, Agent, or Firm*—Tyler A. Stevenson

(57) ABSTRACT

The use is described of compositions comprising (a) (−)-guaiol, (b) further skin-lightening active substance(s) and, optionally, (c) one or more UV-A and/or UV-B absorbers as melanogenesis inhibitors and for skin-lightening.

15 Claims, 1 Drawing Sheet

USE OF GUAIOL FOR TREATING THE SKIN

Figure 1:
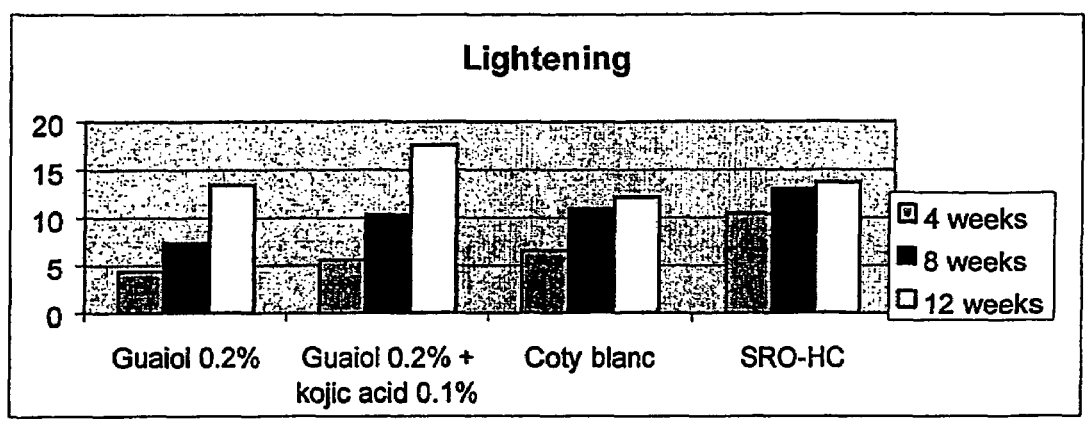

The present invention relates to the use of guaiol from *Callitris intratropica* in mixtures with other components for treating, especially lightening, the skin and as a melanogenesis inhibitor.

Especially in Asian countries there is a strong interest in preparations comprising light-protective filters or mixtures of light-protective filters that preserve the colour of the skin after exposure to sunlight and that, moreover, are capable of giving the skin a lighter appearance by reducing the production of the skin pigment melanin or by lightening the skin.

The problem of the present invention is accordingly to find compositions that prevent tanning of the skin and that, at the same time, are capable of lightening the skin.

It has now been found, surprisingly, that the problem can be solved by mixtures of guaiol and further skin-lightening active substances.

The present invention accordingly relates to the use of compositions comprising
(a) (−)-guaiol and
(b) further skin-lightening active substance(s)

as melanogenesis inhibitors.

The guaiol used in accordance with the invention is preferably obtained as an oil consisting of several fractions from the wood and/or bark of *Callitris intratropica* (Australian Blue Cypress), a species native to relatively warm climatic zones, e.g. Northern Australia, which is cultivated mainly in plantations. The fractions comprise relatively large amounts of (−)-guaiol, which, on cooling, crystallises out from the oil fractions and can be filtered off, centrifuged or isolated from the rest of the oil by decanting.

High-purity guaiol can be obtained from the crude (−)-guaiol by re-crystallisation.

Finely crystalline (−)-guaiol is a sesquiterpene alcohol that corresponds to the formula

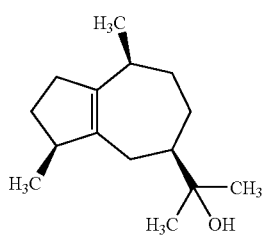

(1)

Guaiol has optical isomers; the compound of formula (1) corresponds to the (−)-form.

The guaiol used in accordance with the invention is preferably obtained by subjecting the raw material of *Callitris intratropica*, which is contaminated with other ingredients, to steam distillation and, in order to purify it further, recrystallising it from a solvent mixture such as, for example, n-hexane/petroleum ether, ethanol/water, dimethylformamide/water, methanol/water, ethylene glycol/water, ethylene glycol methyl and ethyl ester/water, dimethyl sulfoxide/water, tetrahydrofuran/water and dioxane/water. Using that method, purities of >98% w/w can be obtained. Details of obtaining the guaiol used in accordance with the invention can be found in WO 01/53441.

As component (b) there may be used, for example, the following substances or substance classes:
1. γ-Pyrone derivatives corresponding to formula

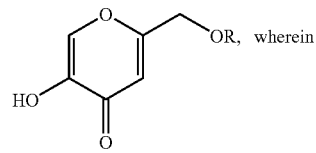

(2)

R is hydrogen (=kojic acid; 5-hydroxy-2-hydroxymethyl-4H-pyran-4-one); or the radical of formula

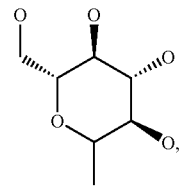

and derivatives thereof such as, for example, kojic acid glucosides.

2. Hydroquinone, also in the form of glycosides, and hydroquinone derivatives in the form of glycosides such as, for example, 4-hydroxyphenyl D-glucopyranoside (=arbutin), corresponding to formula

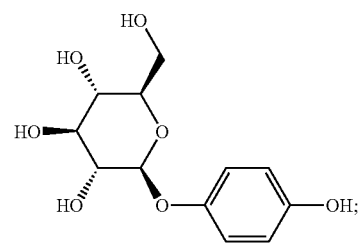

(3)

4-methoxyphenethyl methyl ether; 1,5,9,13-tetramethyl-4,8,12-tetradecatrienyl (9Cl) D-glucopyranoside; 6,10,14-trimethyl-(9Cl)-5,9,13-pentadecatrien-2-ol; 1,5,9,13-tetramethyltetradecyl D-glucopyranoside.

3. Resorcinol derivatives such as glabridin (4-[(3R)-3,4-dihydro-8,8-dimethyl-2H,8H-benzo[1,2-b:3,4-b']dipyran-3-yl]-)1,3-benzenediol or 4-butylresorcinol (=rucinol) 2,4-dihydroxybenzophenones and isomeric benzophenones;
4. L-α-glutamyl-L-cysteinyl-glycine (=glutathione);
5. Alkyldicarboxylic acids such as azelaic acid (nonanedicarboxylic acid) and mono- and di-esters thereof;
6. 1,2-Dihydroxyphenyl derivatives such as, for example, 4-(3,4-dihydroxyphenyl)butan-2-ol; 4-hydroxy-3-methoxybenzylacetone (=gingerone); 2-(3,4-dihydroxyphenyl)-3,5,7-trihydroxy-4H-1-benzopyran-4-one (=quercitin), corresponding to formula

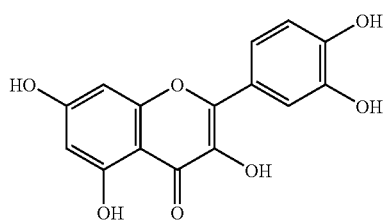

(4)

7. (2,5-Dioxo-4-imidazolidinyl)urea (=allantoin), corresponding to formula

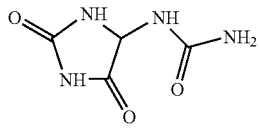

(5)

8. Furanones such as 3-hydroxy-4,5-dimethyl-2(5H)-furanone; 3-hydroxy-4-methyl-5-ethyl-2(5H)-furanone;
9. Phenylacetaldehydes;
10. Benzaldehydes such as, for example, 4-hydroxybenzaldehyde and 3-methylbenzaldehyde;
11. 4-Methoxycinnamaldehydes;
12. Isomeric decenoic acid ($C_{10}H_{18}O_2$);
13. Ascorbic acid and derivatives such as, for example, 6-acylascorbic acid 2-glucoside; sulfates, stearates or phosphates of ascorbic acid;
14. Salicylic acid derivatives such as 6-[(8Z)-8-pentadecenyl]-salicylic acid (anacardic acid monoene) and 6-[(8Z,11Z)-8,11,14-pentadecatrienyl]-salicylic acid (anacardic acid trienes);
15. Phenolic substances such as 3-[8(Z)-pentadecenyl]phenol;
16. Benzo[b]pyran derivatives such as 2,3,7,8-tetrahydroxy-(7Cl, 8Cl, 9Cl)-[1]benzopyrano[5,4,3-cde][1]benzopyran-5,10-dione (=ellagic acid); 2'-hydroxy-2,4,4,7,4'-pentamethylflavan; 2,4,4,4',7-pentamethyl-2'-flavanol acetate; 2-(3,4-dihydro-2,4,4,7-tetramethyl-2H-1-benzopyran-2-yl)-5-methylphenyl and (8β-glycopyranosyl-7-hydroxy-5-methyl-2-(2-oxopropyl)-4H-1-benzopyran-4-one (aloesin), corresponding to formula

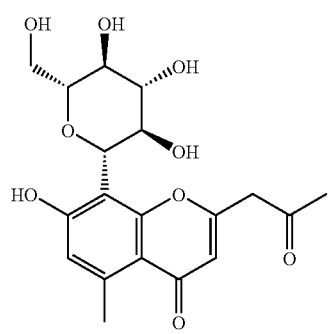

(6)

17. Bornyl and cinnamate derivatives such as endo-1,7,7-trimethylbicyclo[2.2.1]hept-2-yl 3-(4-hydroxyphenyl)-2-propenoate; endo-1,7,7-trimethylbicyclo[2.2.1]hept-2-yl 3-(4-methoxyphenyl)-2-propenoate; 1-methyl-3-(2,2,6-trimethylcyclohexyl)propyl 3-(4-hydroxyphenyl)-2-propenoate; 1-methyl-3-(2,2,6-trimethylcyclohexyl)propyl 3-phenyl-2-propenoate; (1R,2S,4R)-1,7,7-trimethylbicyclo[2.2.1]hept-2-yl 3-[4-(-D-glucopyranosyloxy)phenyl]-2-propenoate.

Preference is given to the use of kojic acid, arbutin, quercitin, aloesin, azelaic acid and esters thereof as component (b).

Each of the above-mentioned inhibitors may be used in the form of single compounds or in the form of mixtures with one another in the composition according to the invention.

It is also possible for more than one of the additional skin-lightening compounds to be used, for example two, three or four further compounds of component (b).

Preferably, the ratio of component (a):(b) is from 1:99, preferably from 5:95, and especially from 10:90, to 99:1, preferably to 95:5, and especially to 90:10, % by weight of component (b).

Special preference is given to mixtures of (a) and (b) wherein the ratio (a):(b) is from 20:80, preferably from 30:70, to 80:20, preferably to 70:30.

The latter compositions may be used, inter alia, for improving the solubility or for increasing the skin-lightening action.

The compositions used in accordance with the invention may further comprise, as component (c), one or more UV-A or UV-B absorbers from the following substance classes:

1. p-aminobenzoic acid derivatives, for example 2-ethylhexyl 4-dimethylaminobenzoate;
2. salicylic acid derivatives, for example 2-ethylhexyl salicylate;
3. benzophenone derivatives, for example 2-hydroxy-4-methoxybenzophenone and its 5-sulfonic acid derivative;
4. dibenzoylmethane derivatives, for example 1-(4-tert-butylphenyl)-3-(4-methoxyphenyl)-propane-1,3-dione;
5. diphenylacrylates, for example 2-ethylhexyl 2-cyano-3,3-diphenylacrylate, and 3-(benzofuranyl) 2-cyanoacrylate;
6. 3-imidazol-4-ylacrylic acid and esters;
7. benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
8. polymeric UV absorbers, for example the benzylidene malonate derivatives described in EP-A-709 080;
9. cinnamic acid derivatives, for example the 2-ethylhexyl 4-methoxycinnamate and isoamyl 4-methoxycinnamate or cinnamic acid derivatives disclosed in U.S. Pat. No. 5,601,811 and WO 97/00851;
10. camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicylo[2.2.1]heptane-1-methanesulfonic acid) and salts, 3-(4'-sulfo)benzylidene-bornan-2-one and salts; camphorbenzalkonium methosulfate;
11. hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethylhexyloxy)-2-hydroxy]-phenyl}-6-[4-(2-methoxyethyl-carboxyl)-phenylamino]-1,3,5-triazine; 2,4-bis{[4-(tris(trimethylsilyloxy-silypropyloxy)-2-hydroxy]-phenyl}-6-(4-methoxyphenyl)-1,3,5-triazine; 2,4-bis{[4-(2"-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2"-methyl-propyloxy)-2-hydroxy]-phenyl}-6-(4-methoxyphenyl)-1,3,5-triazine; 2,4-bis{[4-(3-(2-propyloxy)-2-hydroxy-propyloxy-2-hydroxy]-phenyl}-6-[4-ethylcarboxy)-phenylamino]-1,3,5-triazine;
12. benzotriazole compounds, for example 2,2'-methylene-bis(6-(2H-benzotriazol-2-yl)-4-(1,1,3,3-tetramethylbutyl)-phenol

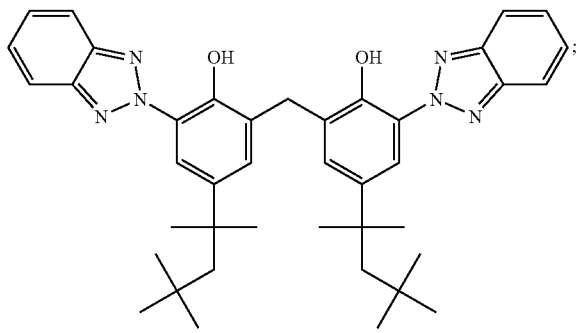

13. trianilino-s-triazine derivatives, for example 2,4,6-trianiline-(p-carbo-2'-ethyl-1'-oxy)-1,3,5-triazine and also the UV absorbers disclosed in U.S. Pat. No. 5,332,568, EP-A-517 104, EP-A-507 691, WO 93/17002 and EP-A-570 838;

14. 2-phenylbenzimidazole-5-sulfonic acid and salts thereof;

15. menthyl o-aminobenzoate;

16. $TiO_2$ (variously encapsulated), ZnO and mica.

The UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Special preference is given to the light-protective agents indicated in the following Table:

| INCI | Chemical Name | CAS No. |
| --- | --- | --- |
| 3-BENZYLIDENE CAMPHOR | 1,7,7-trimethyl-3-(phenylmethylene)-bicyclo[2.2.1]heptan-2-one | 15087-24-8 |
| 4-METHYLBENZYLIDENE CAMPHOR | (+/−)-1,7,7-trimethyl-3-[(4-methylphenyl)-methylene]bicyclo[2.2.1]heptan-2-one | 36861-47-9 |
| BENZOPHENONE-10 | (2-hydroxy-4-methoxyphenyl)-(4-methylphenyl)methanone | 1641-17-4 |
| BENZOPHENONE-1 | 2,4-dihydroxybenzophenone | 131-56-6 |
| BENZOPHENONE-2 | 2,2',4,4'-tetrahydroxybenzophenone | 131-55-5 |
| BENZOPHENONE-3 | 2-hydroxy-4-methoxybenzophenone | 131-57-7 |
| BENZOPHENONE-4 | 2-hydroxy-4-methoxybenzophenone-5-sulfonic acid | 4065-45-6 |
| BENZOPHENONE-6 | 2,2'-dihydroxy-4,4'-dimethoxybenzophenone | 131-54-4 |
| BENZOPHENONE-8 | 2,2'-dihydroxy-4-methoxybenzophenone | 131-53-3 |
| BENZYLIDENE CAMPHOR SULFONIC ACID | alpha-(2-oxoborn-3-ylidene)-toluene-4-sulfonic acid and its salts | 56039-58-8 |
| BUTYL METHOXY-DIBENZOYLMETHANE | 1-[4-(1,1-dimethylethyl)phenyl]-3-(4-methoxyphenyl)propane-1,3-dione | 70356-09-1 |
| CAMPHOR BENZALKONIUM METHOSULFATE | methyl N,N,N-trimethyl-4-[(4,7,7-trimethyl-3-oxobicyclo[2.2.1]hept-2-ylidene)-methyl]anilinium sulfate | 52793-97-2 |
| CINOXATE | 2-ethoxyethyl p-methoxycinnamate | 104-28-9 |
| DEA-METHOXYCINNAMATE | diethanolamine salt of p-methoxy-hydrocinnamate | 56265-46-4 |
| DIISOPROPYL METHYL CINNAMATE | methyl 3-[2,4-bis(1-methylethyl)phenyl]-2-propenoate | 32580-71-5 |
| DIPROPYLENE GLYCOL SALICYLATE | dipropylene glycol salicylate | 7491-14-7 |
| ETHYL DIHYDROXYPROPYL PABA | ethyl 4-bis(2-hydroxypropyl)-amino-benzoate | 58882-17-0 |
| ETHYL DIISOPROPYLCINNAMATE | ethyl 3-[2,4-bis(1-methylethyl)phenyl]acrylate | 32580-72-6 |
| ETHYL METHOXYCINNAMATE | ethyl p-methoxycinnamate | 1929-30-2 |
| GLYCERYL OCTANOATE DIMETHOXYCINNAMATE | | |
| GLYCERYL PABA | glyceryl 1-(4-aminobenzoate) | 136-44-7 |
| HOMOSALATE | 3,3,5-trimethylcyclohexyl-2-hydroxy-benzoate | 118-56-9 |
| ISOAMYL p-METHOXYCINNAMATE | isopentyl p-methoxycinnamate | 71617-10-2 |
| ISOPROPYL DIBENZOYLMETHANE | 1-[4-(1-methylethyl)phenyl]-3-phenyl-propane-1,3-dione | 63250-25-9 |
| ISOPROPYL METHOXYCINNAMATE | isopropyl p-methoxycinnamate | 5466-76-2 |
| LAWSONE | 2-hydroxy-1,4-naphthoquinone | 83-72-7 |
| MENTHYL ANTHRANILATE | menthyl o-aminobenzoate | 134-09-8 |
| MENTHYL SALICYLATE | menthyl salicylate | 89-46-3 |
| OCTOCRYLENE | 2-ethylhexyl 2-cyano-3,3-diphenylacrylate | 6197-30-4 |
| ETHYLHEXYL DIMETHYL PABA | 2-ethylhexyl 4-(dimethylamino)benzoate | 21245-02-3 |
| ETHYLHEXYL METHOXYCINNAMATE | 2-ethylhexyl 4-methoxycinnamate | 5466-77-3 |
| ETHYLHEXYL SALICYLATE | 2-ethylhexyl salicylate | 118-60-5 |
| ETHYLHEXYL TRIAZONE | tris(2-ethylhexyl) 4,4',4''-(1,3,5-triazine-2,4,6-triyltriimino)tris-benzoate; 2,4,6-trianilino-(p-carbo-2'-ethylhexyl-1'-oxy)-1,3,5-triazine | 88122-99-0 |
| PABA | 4-aminobenzoic acid | 150-13-0 |

-continued

| INCI | Chemical Name | CAS No. |
|---|---|---|
| PEG-25 PABA | ethyl 4-aminobenzoate, polymer with oxirane | 113010-52-9 |
| PENTYL DIMETHYL PABA | amyl dimethyl PABA | 14779-78-3 |
| PHENYLBENZIMIDAZOLE SULFONIC ACID | 2-phenyl-1H-benzimidazole-5-sulfonic acid | 27503-81-7 |
| POLYACRYLAMIDOMETHYL BENZYLIDENE CAMPHOR | | 113783-61-2 |
| TEA-SALICYLATE | triethanolamine salicylate | 2174-16-5 |
| TEREPHTHALYLIDENE DICAMPHOR SULFONIC ACID | 3,3'-(1,4-phenylenedimethylene)bis[7,7-dimethyl-2-oxo-bicyclo[2.2.1]heptane-1-methanesulfonic acid] | 90457-82-2 |
| TITANIUM DIOXIDE | titanium dioxide | 13463-67-7 |
| DIGALLOYL TRIOLEATE | digalloyl trioleate | 17048-39-4 |
| ZINC OXIDE | zinc oxide | 1314-13-2 |
| Methylene bis-benzotriazolyl tetramethylbutylphenol | 2,2'-methylene-bis[6-(2H-benzotriazol-2-yl)-4-(1,1,3,3-tetramethylbutyl)-phenol] | 103597-45-1 |
| Bis-ethylhexyloxyphenol methoxyphenyltriazine | 2,4-bis{[4-(2-ethylhexyloxy)-2-hydroxy]-phenyl}-6-(4-methoxyphenyl)-(1,3,5)-triazine | 187393-00-6 |
| BISIMIDAZYLATE | 2,2'-(1,4-phenylene)bis1H-benzimidazole-4,6-disulfonic acid disodium salt | 180898-37-7 |
| DIETHYLHEXYL BUTAMIDO TRIAZONE | bis(2-ethylhexyl) 4,4'-[[6-[[4-[[(1,1-dimethyl-ethyl)amino]carbonyl]phenyl]amino]-1,3,5-triazine-2,4-diyl]diimino]bis-benzoate | 154702-15-5 |
| DROMETRIZOLE TRISILOXANE | 2-(2H-benzotriazol-2-yl)-4-methyl-6-[2-methyl-3-[1,3,3,3-tetramethyl-1-[(trimethylsilyl)oxy]-disiloxanyl]propyl]-phenol | 155633-54-8 |
| BENZYLIDENE MALONATE POLYSILOXANE | alpha-(trimethylsilyl)-omega-(trimethyl-silyloxy)poly[oxy(dimethyl)silylene]-co-[oxy(methyl)(2-{p-[2,2-bis(ethoxy-carbonyl)vinyl]phenoxy}-1-methylene-ethyl)silylene]-co-[oxy(methyl)(2-{p-[2,2-bis(ethoxycarbonyl)vinyl]phenoxy}prop-1-enyl)silylene] | 207574-74-1 |
| | hexyl 2-(4-diethylamino-2-hydroxybenzoyl)-benzoate | 302776-68-7 |

Each of the above-mentioned light-protective agents, especially the light-protective agents in the above Table indicated as being preferred, can be used in admixture with the UV absorbers according to the invention. It will be understood in that connection that, in addition to the UV absorbers according to the invention, it is also possible for more than one of the additional light-protective agents to be used, for example, two, three, four, five or six further light-protective agents. Preference is given to the use of mixing ratios of UV absorbers according to the invention/further light-protective agents of from 1:99 to 99:1, especially from 1:95 to 95:1 and preferably from 10:90 to 90:10, based on weight. Of special interest are mixing ratios of from 20:80 to 80:20, especially from 40:60 to 60:40 and preferably of approximately 50:50. Such mixtures can be used, inter alia, to improve solubility or to increase UV absorption.

Appropriate mixtures can be used especially advantageously in the cosmetic composition according to the invention.

In the composition used in accordance with the invention there are preferably used, as component (c), triazine UV absorbers of formula

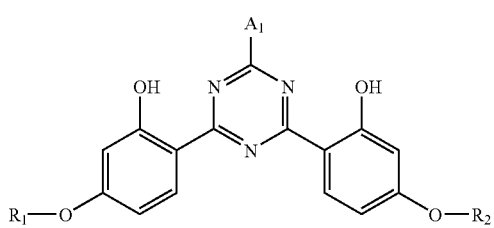

(2)

wherein $R_1$ and $R_2$ are each independently of the other $C_3$-$C_{18}$alkyl; $C_2$-$C_{18}$alkenyl; a radical of formula —$CH_2$—$CH(—OH)$—$CH_2$—O—$T_1$; or $R_1$ and $R_2$ are a radical of formula

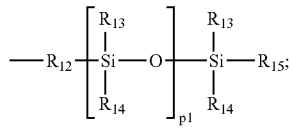

$R_{12}$ is a direct bond; a straight-chain or branched $C_1$-$C_4$alkylene radical or a radical of formula —$C_{m_1}H_{2m_1}$— or —$C_{m_1}H_{2m_1}$—O—;

$R_{13}$, $R_{14}$ and $R_{15}$ are each independently of the others $C_1$-$C_{18}$alkyl; $C_1$-$C_{18}$alkoxy or a radical of formula

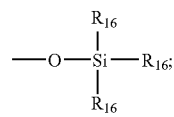

$R_{16}$ is $C_1$-$C_5$alkyl;

$m_1$ and $m_3$ are each independently of the other from 1 to 4;

$p_1$ is 0 or a number from 1 to 5;

$A_1$ is a radical of formula

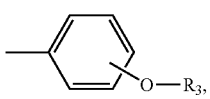 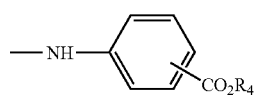

or of formula

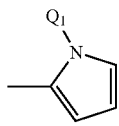

$R_3$ is hydrogen; $C_1$-$C_{10}$alkyl; —$(CH_2CHR_5$—$O)_{n_1}$—$R_4$; or a radical of formula —$CH_2$—$CH(—OH)$—$CH_2$—$O$—$T_1$;

$R_4$ is hydrogen; M; $C_1$-$C_5$alkyl; or a radical of formula —$(CH_2)_{m_2}$—$O$—$T_1$;

$R_5$ is hydrogen; or methyl;

$T_1$ is hydrogen; or $C_1$-$C_8$alkyl;

$Q_1$ is $C_1$-$C_{18}$alkyl;

M is a metal cation;

$m_2$ is from 1 to 4; and $n_1$ is 1-16.

Special preference is given to the compounds of formulae

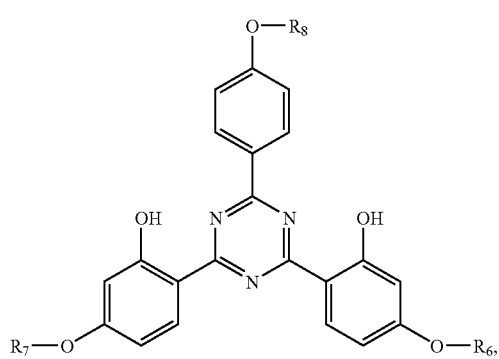

(3a)

(3b)

(4a)

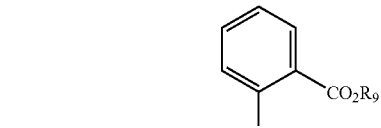

-continued (4b)

wherein $R_6$ and $R_7$ are each independently of the other $C_3$-$C_{18}$alkyl; or —$CH_2$—$CH(—OH)$—$CH_2$—$O$—$T_1$;

$R_8$ is $C_1$-$C_{10}$alkyl or a radical of formula

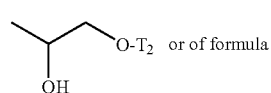 (3a$_1$)

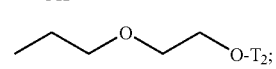 (3a$_2$)

$R_9$ is hydrogen; M; $C_1$-$C_5$alkyl; or a radical of formula —$(CH_2)_m$—$O$—$T_2$;

$T_1$ and $T_2$ are each independently of the other hydrogen; or $C_1$-$C_5$alkyl; and m is from 1 to 4.

At the forefront of interest are compounds of formulae (3a) and (3b) wherein $R_6$ and $R_7$ are each independently of the other $C_3$-$C_{18}$alkyl; or —$CH_2$—$CH(—OH)$—$CH_2$—$O$—$T_1$;

$R_8$ is $C_1$-$C_{10}$alkyl;

and also compounds of formulae (4a) and (4b) wherein $R_6$ and $R_7$ are each independently of the other $C_3$-$C_{18}$alkyl or —$CH_2$—$CH(—OH)$—$CH_2$—$O$—$T_1$; and $T_1$ is hydrogen; or $C_1$-$C_5$alkyl.

As examples of compounds of formula (2) there may be mentioned:

2-(4'-methoxyphenyl)-4,6-bis(2'-hydroxy-4'-n-octyloxyphenyl)-1,3,5-triazine;

2,4-bis{[4-(3-(2-propyloxy)-2-hydroxy-propyloxy)-2-hydroxy]-phenyl}-6-(4-methoxyphenyl)-1,3,5-triazine;

2,4-bis{[4-(2-ethyl-hexyloxy)-2-hydroxy]-phenyl}-6-[4-(2-methoxyethyl-carboxyl)-phenylamino]-1,3,5-triazine;

2,4-bis{[4-(tris(trimethylsiloxy-silylpropyloxy)-2-hydroxy]-phenyl}-6-(4-methoxyphenyl)-1,3,5-triazine;

2,4-bis{[4-(2"-methylpropenyloxy)-2-hydroxy]-phenyl}-6-(4-methoxyphenyl)-1,3,5-triazine;

2,4-bis{[4-(1',1',1',3',5',5',5'-heptamethyltrisilyl-2"-methylpropyloxy)-2-hydroxy]-phenyl}-6-(4-methoxyphenyl)-1,3,5-triazine;

2,4-bis{[4-(3-(2-propyloxy)-2-hydroxy-propyloxy)-2-hydroxy]-phenyl}-6-[4-ethylcarboxyl)-phenylamino]-1,3,5-triazine; or 2,4-bis{[4-(2-ethyl-hexyloxy)-2-hydroxy]-phenyl}-6-(1-methylpyrrol-2-yl)-1,3,5triazine.

Very special preference is given to those triazine compounds of formula (3) or (4) wherein $R_6$ and $R_7$ have the same meaning, and especially to the compound of formula

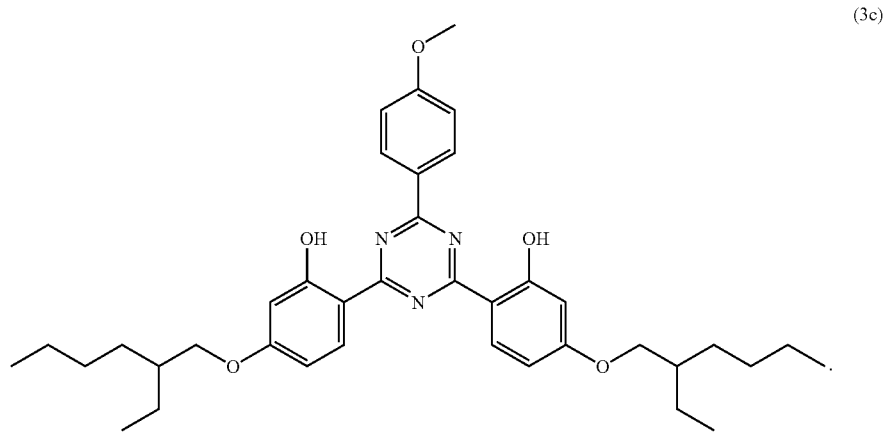

(3c)

In accordance with the invention there are also used, as organic UV absorbers, benzotriazole compounds of formula

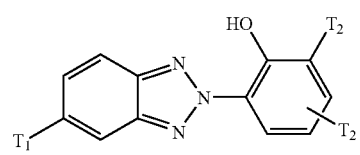

(5)

wherein $T_1$ is hydrogen; or $C_1$-$C_3$alkyl and $T_2$ is unsubstituted $C_1$-$C_4$alkyl, preferably tert-butyl, or phenyl-substituted $C_1$-$C_4$alkyl, preferably α,α-dimethylbenzyl.

Preferred triazole compounds used in accordance with the invention correspond to formula

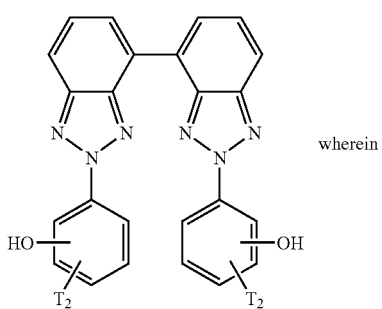

(6)

wherein $T_2$ is hydrogen; or $C_1$-$C_{12}$alkyl, preferably iso-octyl.

Preference is further given to the use of benzotriazole compounds of formula

(7)

wherein $T_2$ is $C_1$-$C_{12}$alkyl, preferably iso-octyl.

Further preferred compounds used in accordance with the invention that correspond to component (c) are octyl methoxycinnamate or benzophenone 3.

The invention relates also to cosmetic formulations comprising (a) (−)-guaiol, (b) further skin-lightening active substance(s) and, optionally, (c) one or more UV-A and/or UV-B absorbers.

The cosmetic formulations according to the invention preferably contain (a) from 0.01 to 5% by weight, preferably from 0.05 to 1% by weight, (−)-guaiol, (b) from 0.01 to 5% by weight, preferably from 0.05 to 1% by weight, further skin-lightening active substance(s) and, optionally, (c) from 0 to 30% by weight, preferably from 0.1 to 15% by weight, one or more UV-A and/or UV-B absorbers.

Table 1 below sets out Examples of mixtures of (−)-guaiol (component (a)) with further skin-lightening active substances (component (b)) and UV absorbers (component (c)). The figures are based on percentages by weight in the final cosmetic formulation.

TABLE 1

| Component [CAS No.] (max. conc.) | Formulation | | | | | | | | | |
|---|---|---|---|---|---|---|---|---|---|---|
| | C1 | C2 | C3 | C4 | C5 | C6 | C7 | C8 | C9 | C10 |
| Component (a) (total) | 0.05 | 0.1 | 0.1 | 0.1 | 0.2 | 0.3 | 0.3 | 0.3 | 0.5 | 1 |
| 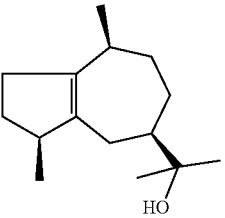 guaiol [489-86-1] | 0.05 | 0.1 | 0.1 | 0.12 | 0.2 | 0.3 | 0.3 | 0.3 | 0.5 | 1 |
| Components (b) (total) | 0.1 | 0.2 | 0.4 | 0.2 | 0.1 | 0.2 | 0.3 | 0.5 | 0.3 | 5 |
| 5-HYDROXY-2-HYDROXY-METHYL-4H-PYRAN-4-ONE (= KOJIC ACID) [501-30-4] | 0.05 | 0.1 | 0.2 | | 0.1 | | | 0.2 | 0.3 | |
| 4-HYDROXYPHENYL β-D-GLUCO-PYRANOSIDE (= ARBUTIN) [497-76-7] | 0.05 | | 0.1 | 0.2 | | 0.1 | | 0.3 | | 2 |
| (2,5-DIOXO-4-IMIDAZOLIDINYL)-UREA (= ALLANTOIN) [97-59-6] | | 0.1 | | | | | 0.1 | | | |
| 2-(3,4-DIHYDROXY-PHENYL)-3,5,7-TRIHYDROXY-4H-1-BENZOPYRAN-4-ONE (= QUERCITIN) [117-39-5] | | | 0.1 | | | 0.1 | | | | |
| 1,7-HEPTANE-DICARBOXYLIC ACID (= AZELAIC ACID) [123-99-9] | | | | | | | | 0.2 | | 3 |
| Component (c) (total) | 30 | 25 | 15 | 25 | 20 | 0 | 35 | 15 | 20 | 10 |
| 3-(2H-BENZO-TRIAZOL-2-YL)-4-HYDROXY-5-(1-METHYL-PROPYL)-BENZENESULFONIC ACID MONOSODIUM SALT [92484-48-5] | 5 | | | | 5 | | | | | |
| PROPYL GALLATE [121-79-9] | 2 | | | | | | 5 | | | 2 |
| N-[3-(3,5-DI-TERT-BUTYL-4-HYDROXY-PHENYL)PROPIONYL] SULFANILIC ACID (OR SALTS E.G. WITH SODIUM) | | 10 | 5 | | | | | | | |
| BENZYLIDENEMALO-NATE POLYSILOXANE [207574-74-1] | 10 | | | | 2 | | | | | |
| DROMETRIZOLE TRISILOXANE [155633-54-8] (15) | 5 | | | | | | 5 | | | |
| DIETHYLHEXYL BUTAMIDO TRIAZONE [154702-15-5] (10) | | | | | | | | | 5 | |
| 2,2'-[6-(4-METHOXY-PHENYL)-1,3,5-TRIAZINE-2,4-DIYL]-BIS[5-((2-ETHYL-HEXYL)-OXY]-PHENOL [187393-00-6] (10) | | | 5 | 10 | | | | 5 | | |

TABLE 1-continued

| Component [CAS No.] (max. conc.) | C1 | C2 | C3 | C4 | C5 | C6 | C7 | C8 | C9 | C10 |
|---|---|---|---|---|---|---|---|---|---|---|
| 2,2'-(1,4-PHENYLENE)-BIS-1H-BENZIMIDAZOLE-4,6-DISULFONIC ACID DISODIUM SALT [180898-37-7] (10) | | | 5 | 5 | | | | | | |
| BIS-BENZOTRIAZOLYL TETRAMETHYLBUTYLPHENOL [103597-45-1] (10) | | | | | 5 | | 5 | 5 | | |
| TEREPHTHALYLIDENE DICAMPHOR SULFONIC ACID [90457-82-2] (10) | | | | | 8 | | | | | |
| POLYACRYLAMIDOMETHYL BENZYLIDENE CAMPHOR [113783-61-2] (6) | | | | | | | 5 | | | |
| PHENYLBENZIMIDAZOLE SULFONIC ACID [27503-81-7] (8) | | 5 | | | | | | | | |
| ETHYLHEXYL METHOXYCINNAMATE [5466-77-3] (10) | | 5 | | 5 | | | 8 | | | |
| OCTOCRYLENE [6197-30-4] (10) | | | | | 5 | | | | | |
| CAMPHOR BENZALKONIUM METHOSULFATE [52793-97-2] (6) | | | | | | | 2 | | 2 | |
| BUTYL METHOXYDIBENZOYLMETHANE [70356-09-1] (5) | 3 | | | | | | | 5 | | |
| BENZOPHENONE-3 [131-57-7] (10) | 2 | | | | | | 5 | | | |
| BENZOPHENONE-4 [4065-45-6] (5) | 2 | | | | | | | | 3 | |
| N-[3-[[4-(DIMETHYLAMINO)-BENZOYL]-AMINO]PROPYL]-N,N-DIMETHYL-1-DODECANAMINIUM SALT WITH 4-METHYL-BENZENESULFONIC ACID [156679-41-3] | | 3 | | | | | | | | 3 |
| N,N,N-TRIMETHYL-3-((1-OXO-3-PHENYL-2-PROPENYL)AMINO]-1-PROPANAMINIUM CHLORIDE [177190-98-6] | | 2 | | | | | | | 5 | |
| 3-BENZYLIDENE CAMPHOR [15087-24-8] (2) | | | | | | | | | 2 | |
| 4-METHYLBENZYLIDENE CAMPHOR [36861-47-9] (4) | | | | | | | | | 3 | |
| BENZYLIDENE CAMPHOR SULFONIC ACID [56039-58-8] (6) | | | | | | | | | | 5 |

The cosmetic formulations are suitable for protecting ultraviolet-sensitive organic materials, especially the skin, against the damaging effect of UV radiation, especially for lightening the skin in conjunction with one or more UV filter(s), that is to say during or after simultaneous lightening of the skin.

The compositions according to the invention may be used both in dissolved form and in the micronised state.

Any known process suitable for the preparation of microparticles can be used for the preparation of the micronised guaiol or of the composition according to the invention, for example:

wet-grinding with a hard grinding medium, for example zirconium silicate and a protective surfactant or a protective polymer in water or in a suitable organic solvent;

spray-drying from a suitable solvent, for example aqueous suspensions or suspensions containing organic solvents, or true solutions in water, ethanol, dichloroethane, toluene, N-methylpyrrolidone inter alia;

by the expansion, according to the RESS process (Rapid Expansion of Supercritical Solutions), of supercritical fluids (e.g. $CO_2$) in which the UV filter or filters is/are dissolved or by the expansion of fluid carbon dioxide together with a solution of one or more UV filters in a suitable organic solvent;

by reprecipitation from suitable solvents, including supercritical fluids (GASR process=Gas Anti-Solvent Rcrystallisation/PCA process=Precipitation with Ccompressed Antisolvents).

As grinding apparatus for the preparation of the micronised organic skin-lightening substances and substance mixtures there may be used, for example, a jet mill, ball mill, vibratory mill or hammer mill, preferably a high-speed mixing mill. The grinding is preferably carried out with a grinding aid, for example an alkylated vinylpyrrolidone polymer, a vinylpyrrolidone/vinyl acetate copolymer, an acyl glutamate, an alkyl polyglucoside, ceteareth-25 or, especially, a phospholipid.

The micronised individual components present in the composition according to the invention usually have an average particle size of from 0.02 to 2, preferably from 0.05 to 1.5, and more especially from 0.1 to 1.0, nm.

The micronised individual components present in the composition according to the invention can also be used dry in powder form or in crystals (obtained by recrystallisation). For that purpose the individual components are subjected to known grinding methods, such as vacuum atomisation, countercurrent spray-drying etc. Such powders have a particle size of from 0.1 nm to 2 µm. To avoid agglomeration processes, the individual components can be coated with a surface-active compound prior to the pulverisation process, for example with an anionic, non-ionic or amphoteric surfactant, e.g. a phospholipid or a known polymer, such as PVP, an acrylate etc. Crystallisation is possible from n-hexane, acetone or lower alcohols in admixture with water from the boiling heat.

The cosmetic compositions can be prepared by physically mixing components (a) and (b) and, optionally, (c) with the adjuvant using customary methods, for example by simply stirring together the individual components. The UV absorber can be used therein, for example, without further treatment, or in the micronised state, or in the form of a powder.

The cosmetic compositions may be, for example, creams, gels, lotions, alcoholic and aqueous/alcoholic solutions, emulsions, wax/fat compositions, stick preparations, powders or ointments.

As water- and oil-containing emulsions (e.g. W/O, O/W, O/W/O and W/O/W emulsions or microemulsions) the compositions contain, for example, from 0.1 to 30% by weight, preferably from 0.1 to 15% by weight and especially from 0.5 to 10% by weight, based on the total weight of the composition, of component (a), (b) and, optionally, (c), from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

As oil components of oil-containing compositions (e.g. oils, W/O, O/W, O/W/O and W/O/W emulsions or microemulsions) there come into consideration, for example, Guerbet alcohols based on fatty alcohols having from 6 to 18, preferably from 8 to 10, carbon atoms, esters of linear $C_6$-$C_{24}$ fatty acids with linear $C_3$-$C_{24}$ alcohols, esters of branched $C_6$-$C_{13}$carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/tri-glyceride mixtures based on $C_6$-$C_{18}$ fatty acids, esters of C6-$C_{24}$ fatty alcohols and/or Guerbet alcohols with aromatic carboxylic acids, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxyl groups, vegetable oils (such as sunflower oil, olive oil, soybean oil, rapeseed oil, almond oil, jojoba oil, orange oil, wheatgerm oil, peach kernel oil and the liquid components of coconut oil), branched primary alcohols, substituted cyclohexanes, linear and branched $C_6$-$C_{12}$ fatty alcohol carbonates, Guerbet carbonates, esters of benzoic acid with linear and/or branched $C_6$-$C_{22}$alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure cleavage of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmityl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2- ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or tri-valent metal salts (alkaline earth metal, $Al^{3+}$ inter alia) of one or more alkylcarboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the compositions.

As emulsifiers there come into consideration, for example, non-ionic surfactants from the following groups:

- addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;
- $C_{12}$-$C_{22}$ fatty acid mono- and di-esters of addition products of from 1 to 30 mol of ethylene oxide with polyols having from 3 to 6 carbon atoms, especially with glycerol;
- glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;
- $C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;
- addition products of from 2 to 60 mol, especially from 15 to 60 mol, of ethylene oxide with castor oil and/or hydrogenated castor oil;
- polyol esters and especially polyglycerol esters, for example diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable;
- partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2diricinoleates;
- mono-, di- and tri-alkylphosphates and also mono-, di- and/or tri-PEG-alkylphosphates and salts thereof;
- wool wax alcohols;
- one or more ethoxylated esters of natural derivatives, for example polyethoxylated esters of hydrogenated castor oil;
- silicone oil emulsifiers, for example silicone polyol;
- polysiloxane/polyalkyl/polyether copolymers and corresponding derivatives, for example cetyl dimethicone copolyol;
- mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates and also
- polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include mono-glycosides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethyl-imidazolines, each having from 8 to 18 carbon atoms in the alkyl or acyl group, and also cocoacylaminoethylhydroxyethylcarboxymethylglycinate.

Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$ $C_{18}$-alkyl or -acyl group, contain at least one free amino group and at least one —COOH or —$SO_3H$ group in the molecule and are capable of forming internal salts.

Examples of suitable ampholytic surfactants include N-alkylglycines, N-alkylpropionic acids, N-alkylaminobutyric acids, N-alkyliminodipropionic acids, N-hydroxyethyl-N-alkylamido-propylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylamino-propionate, cocoacylaminoethylaminopropionate and $C_{12}$-$C_{18}$acylsarcosine. In addition to the ampholytic emulsifiers there also come into consideration quaternary emulsifiers, special preference being given to those of the esterquat type, preferably methylquatemised di-fatty acid triethanolamine ester salts.

Non-ionic emulsifiers are preferred. Of the non-ionic emulsifiers mentioned, special preference is given to ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, further UV light-protective factors, antioxidants, hydrotropic agents, preservatives, insect repellents, solubilisers, perfume oils, colourants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Examples of suitable mild surfactants, that is to say surfactants especially well tolerated by the skin, that may be mentioned include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

As pearlescent waxes there come into consideration, for example: alkylene glycol esters, especially ethylene glycol distearate; fatty acid alkanolamides, especially coco fatty acid diethanolamide; partial glycerides, especially stearic acid monoglyceride; esters of unsubstituted or hydroxy-substituted polycarboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

As consistency regulators there come into consideration especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methyl-glucamides of the same chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oglioglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolysed collagen (Lamequat®/L/Grünau), quaternised wheat polypeptides, polyethyleneimine, cationic silicone polymers, for example amidonethicones, copolymers of adipic acid and dimethylaminohydroxypropyldiethylene-triamine (Cartaretin®/Sandoz), copolymers of acrylic acid with dimethyldiallymmonuim chloride (Merquat® 550/Chemviron), polyaminopolyamides, as described, for example, in FR-A-2 252 840, and the crosslinked water-soluble polymers thereof, cationic chitin derivatives, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

As anionic, zwitterionic, amphoteric, and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters therefor, uncrosslinked polyacrylic acids and polyacrylic acids crosslinked with polyols, acrylamidopropyltrimethylammonium chloride/-acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolione/dimethylaminoethyl methacrylate/vinyl caprolactam terpolymers and also optionally derivatised cellulose ethers and silicones.

Suitable silicone compounds are, for example, dimethylpolysiloxanes, methylphenyl-polysilanes, cyclic silicones, and also amino-, fatty acid-, alcohol-, polyether-, expoxy-, fluorine-, glycoside-, and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils, and fatty acid esters or microwaxes solid at room temperature optionally in combination with hydrophilic waxes, e.g. cetylstearyl alcohol or partial glycerides. Metals salts of fatty acids, for example magnesium, aluminium and/or zinc stearate or ricinoleate, may be used as stabilisers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthanol, AHA acids, amino acids, ceramides, pseudoceramides, essential oils, plant extracts and vitamin complexes.

As deodorising active ingredients there come into consideration, for example, anti-perspirants, for example aluminium chlorohydrates, those being colourless hygroscopic crystals which deliquesce readily in air and are obtained on evaporation of aqueous aluminium chloride solutions. Aluminium chlorohydrate is used for preparations of perspiration-inhibiting and deodorising preparations and probably acts by partially closing the sweat glands as a result of protein and/or polysaccharide precipitation (see J. Soc. Cosm. Chem. 24, 281 (1973)). Under the trade mark Locron® of Hoechst AG, Frankfurt (FRG), there is available commercially, for example, an aluminum chlorohydrate corresponding to formula $Al_2(OH)_5Cl \times 2.5\ H_2O$, the use of which is especially preferred (see J. Pharm. Pharmacol. 26, 531 (1975)). Besides the chlorohydrates, it is also possible to use aluminium hydroxy-acetates and acidic aluminum/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG). The substances inhibit enzymes activity and hence reduce of our formation, probably with the free acid being released as a result of cleavage of the citric acid ester and reducing the pH on the skin to such an extent that the enzymes are inhibited as a result. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid ot tataric acid diethyl ester. Antibacterial active ingredients that influence the microbial flora and kill, or inhibit the growth of, perspiration-decomposing bacteria can likewise be present in the preparations (especially in stick preparations). Examples include chitosan, phenocxyethanol, chlorhexidine gluconate and 4-(2-tert-butyl-5-methylphenoxy) phenol. 5-Chloro-2-(2,4-dichlorophenoxy)-phenol (Irgansan®, Ciba Specialty Chemicals Inc.) has also proved especially effective.

In the compositions according to the invention, it is also possible to use, in addition to components (a), (b) and (c), secondary light-protective agents of the antioxidant kind which interrupt the photochemical reaction chain triggered when UV radiation penetrates the skin or hair. That property is desirable for cosmetic light protection because, as a result of the influence of UV and light, damaging radicals may be formed both in formulations and on the skin. Providing the compositions according to the invention with antioxidants achieves not only protection form UV damage but also, at the same time, protection from the photochemical degradation of constituents in the formulation. Typical examples of such antioxidants are:

amino acids (e.g. glycine, histidine, tyrosine, trytophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, (e.g. α-carotene, β-carotene, lycopene) and derivatives thereof, chlorogenic acid and derivatives thereof, lipoic acid and derivatives thereof (e.g. dihydrlipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, α-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides, and salts) and also sulfoximine compounds (e.g. buthionine sulfoximines, homocysteine sulfoximine, buthionine sulfones, penta-, hexa-, hepta-thionine sulfoximine) in very small tolerable amounts, also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. α-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherals and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients.

Mentioned may also be made of the phenolic antioxidants listed in the following Table.

TABLE 2

| Compound of formula | |
| --- | --- |
| (AO 1) | [structure: bis-phenol with two OH groups, two tert-butyl groups, and two $CH_3$ groups, linked by a methylene bridge] |

TABLE 2-continued

| Compound of formula | |
|---|---|
| (AO 2) | [3,5-di-tert-butyl-4-hydroxyphenyl-(CH₂)₂-C(=O)-O-(CH₂)₃-]₂ |
| (AO 3) | 3-(3,4-dimethylphenyl)-5,7-di-tert-butyl-benzofuran-2(3H)-one |
| (AO 4) | [3,5-di-tert-butyl-4-hydroxyphenyl-(CH₂)₂-C(=O)-NH-(CH₂)₃-]₂ |
| (AO 5) | [3,5-di-tert-butyl-4-hydroxyphenyl-(CH₂)₂-C(=O)-NH-(CH₂)₃-]₂ |
| (AO 6) | bis(3-tert-butyl-5-methyl-4-hydroxy-2-methylphenyl)butane |
| (AO 7) | 1,2,4,5-tetramethyl-3,6-bis(R)-benzene; R = —CH₂—(3,5-di-tert-butyl-4-hydroxyphenyl) |

TABLE 2-continued
| Compound of formula | |
|---|---|
| (AO 8) | 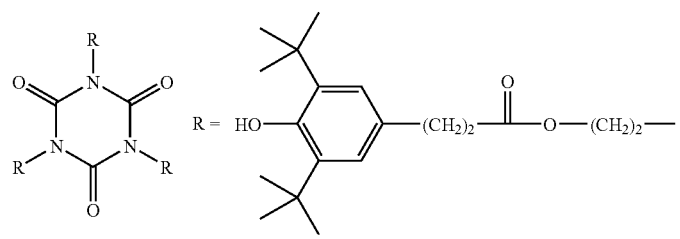 |
| (AO 9) | 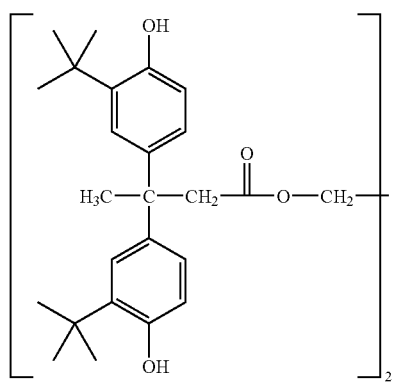 |
| (AO 10) | 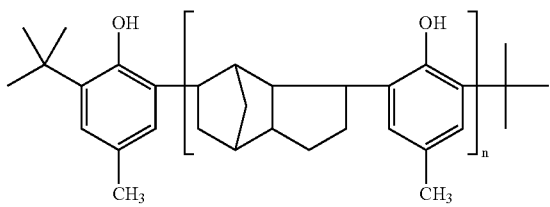<br>n = 1–3 |
| (AO 11) | 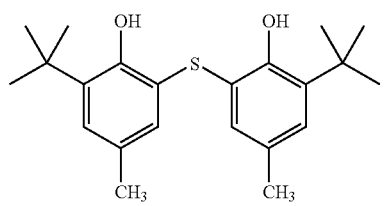 |
| (AO 12) | 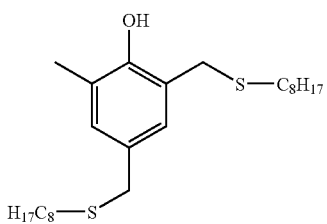 |

TABLE 2-continued
| Compound of formula | |
|---|---|
| (AO 13) | 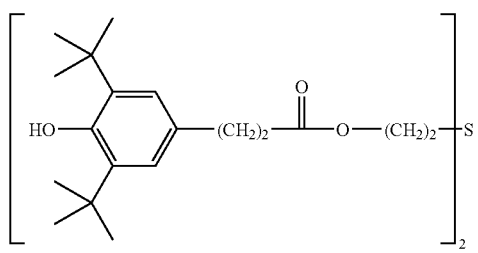 |
| (AO 14) | 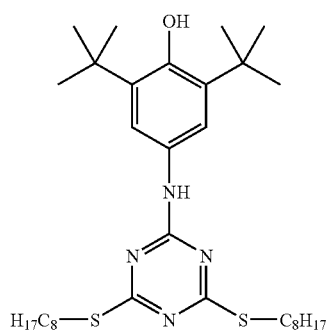 |
| (AO 15) | 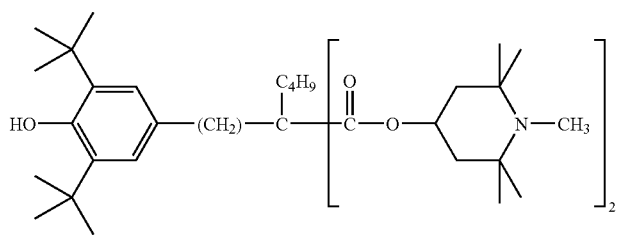 |
| (AO 16) | 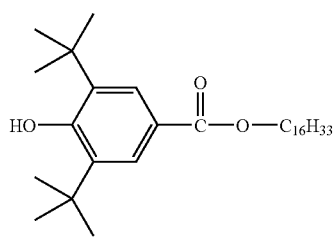 |
| (AO 17) | 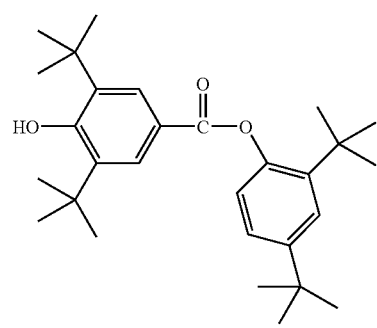 |

TABLE 2-continued
| Compound of formula | |
|---|---|
| (AO 18) | 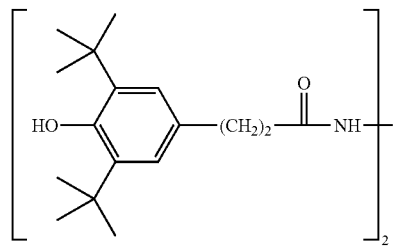 |
| (AO 19) | 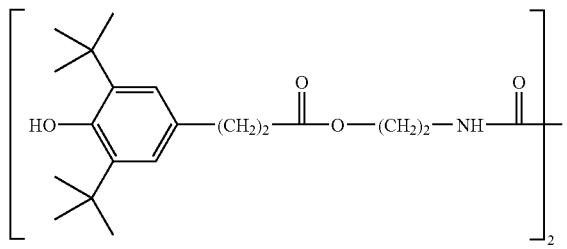 |
| (AO 20) | 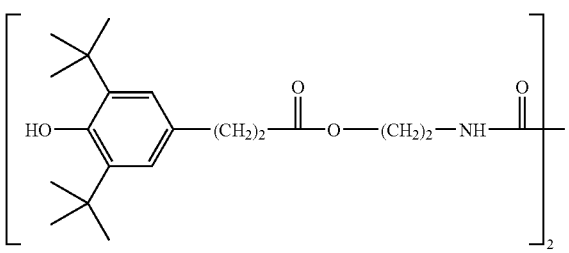 |
| (AO 21) | 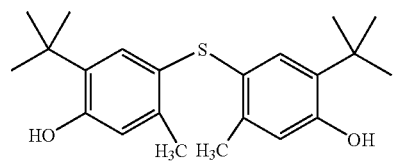 |
| (AO 22) | 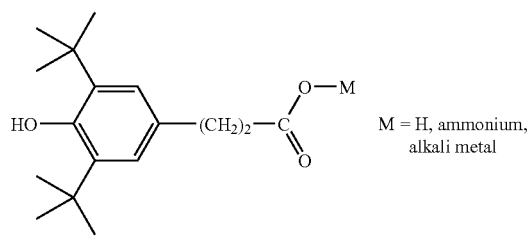 M = H, ammonium, alkali metal |
| (AO 23) | 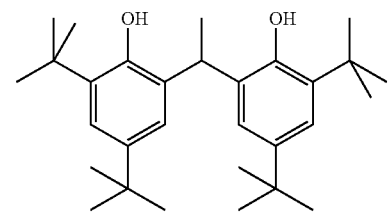 |

TABLE 2-continued

| Compound of formula | |
|---|---|
| (AO 24) | [structure: methylenebis(di-tert-butyl-methylphenol)] |
| (AO 25) | [structure: 3,5-di-tert-butyl-4-hydroxyphenyl-(CH₂)₂-C(O)-NH-C₆H₄-SO₃M]   M = H, Na |
| (AO 26) | [structure: [3,5-di-tert-butyl-4-hydroxyphenyl-(CH₂)₂-C(O)-O-CH₂-]₄C] |
| (AO 27) | [structure: 3,5-di-tert-butyl-4-hydroxyphenyl-(CH₂)₂-C(O)-O-C₁₈H₃₇] |
| (AO 28) | [structure: tetrakis(3,5-di-tert-butyl-4-hydroxybenzyl)-methylbenzene type] |

Also suitable for the composition according to the invention are sterically hindered amines (also called HALS compounds (="Hindered Amine Light Stabilizers")).

Those compounds are preferably 2,2,6,6-tetraalkylpiperidine derivatives.

Examples of tetraalkylpiperidine derivatives that may be used in accordance with the invention can be found in EP-A-356 677, pages 3-17, sections a) to f). The said sections of that EP-A are to be considered as part of the present description. Especially advantageously, the following tetraalkylpiperidine derivatives are used:

bis(2,2,6,6-tetramethylpiperidin-4-yl)sebacate, bis(2,2,6,6-tetramethyl-piperidin-4-yl)-succinate, bis(1,2,2,6,6-pentamethylpiperidin-4-yl)sebacate, bis(1-octyloxy-2,2,6-6- tetramethylpiperidin-4-yl)sebacate, n-butyl-3,5-di-tert-butyl-4-hydroxybenzyl-malonic acid bis(1,2,2,6,6-pentamethylpiperidyl) ester, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyl-oxy-2,2,6,6-tetramethylpiperidyl)sebacate, bis(1-octyloxy-2,2,6,6-tetramethylpiperidyl)-succinate, the condensation product of N,N'-bis(2,2,6,6-tetramethyl-4-piperidyl)-hexamethylenediamine and 4-morpholino-2,6-dichloro-1,3,5-triazine, the condensation product of 2-chloro-4,6-di(4-n-butylamino-2,2,6,6-tetramethylpiperidyl)-1,3,5-triazine and 1,2-bis(3-aminopropylamino)ethane, the condensation product of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)-pyrrolidine-2,5-dione, 3-dodecyl-1-(1,2,2,6,6-pentamethyl-4-piperidyl)-pyrrolidine-2,5-dione, mixture of 4-hexadecyloxy- and 4-stearyloxy-2,2,6,6-tetramethylpiperidine, -2,6-dichoro-13,5-triazine, the condensation product of 1,2-bis(3-aminopropylamino)ethane and 2,4,6-trichloro-1,3,5-triazine and 4-butylamino-2,2,6,6-tetramethylpiperidine (CAS Reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4.5]decane, the reaction product of 7,7,9,9-tetramethyl-2-cycloundecyl-1-oxa-3,8-diaza-4-oxospiro[4.5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]henicosane, 8-acetyl-3-dodecyl-1,3,8-triaza-7,7,9,9-tetramethylspiro-[4.5]decane-2,4-dione, or a compound of formula

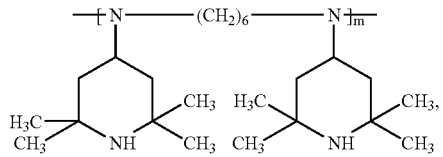

wherein m has a value of 5–50,

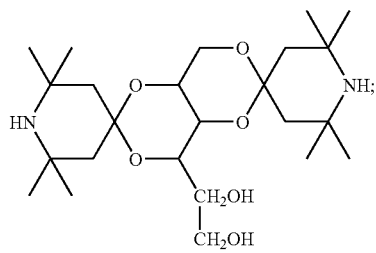

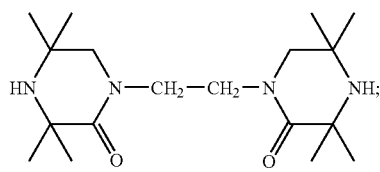

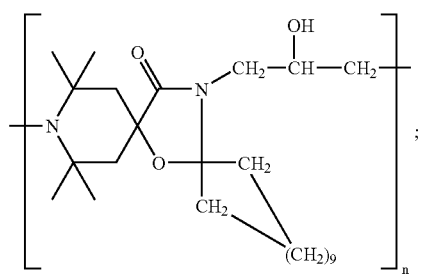

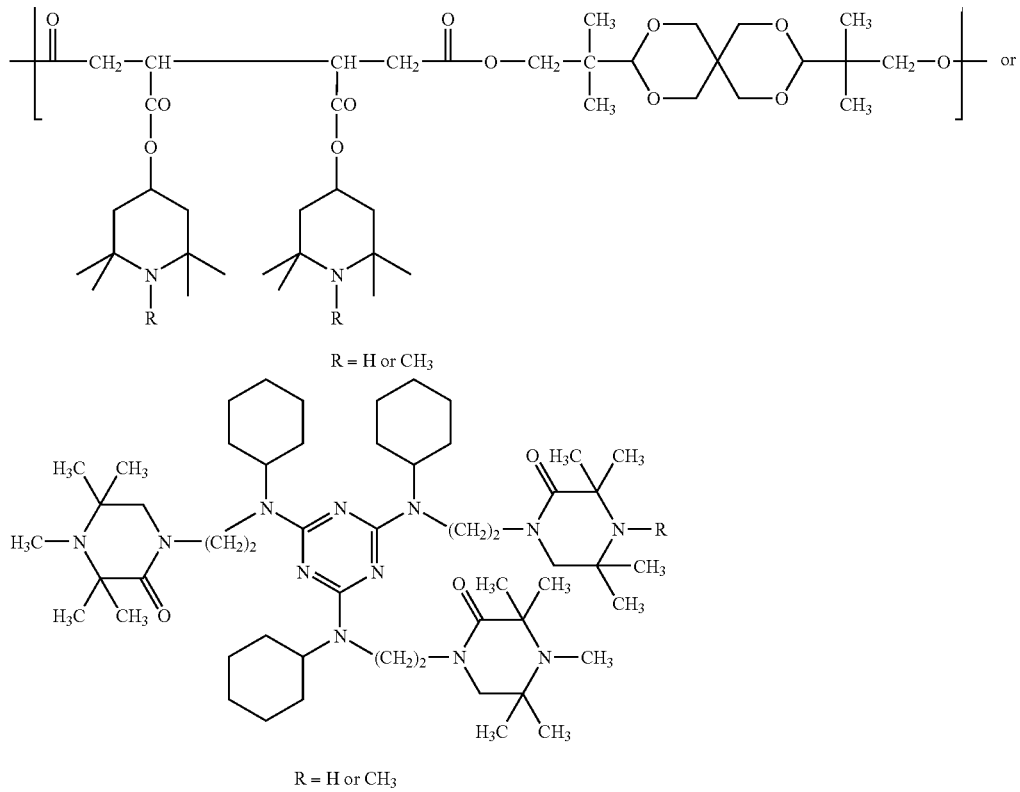

The amount of antioxidants is usually from 0.001 to 30% by weight, preferably from 0.01 to 3% by weight, based on the weight of the composition according to the invention.

To improve the flow behavior it is also possible to employ hydrotropic agents, for example ethanol, isopropyl alcohol or polyols. The polyols that come into consideration for that purpose have preferably from 2 to 15 carbon atoms and at least two hydroxy groups. The polyols may also contain further functional groups, especially amino groups, and/or may be modified with nitrogen. Typical examples are as follows:
  glycerol;
  alkylene glycols, for example ethylene glycol, diethylene glycol, propylene glycol, butylene glycol, hexylene glycol and also polyethylene glycols having an average molecular weight of from 100 to 1000 Dalton;
  technical oligoglycerol mixtures having an intrinsic degree of condensation of from 1.5 to 10, for example technical diglycerol mixtures having a diglycerol content of from 40 to 50% by weight;
  methylol compounds, such as, especially, trimethylolethane, trimethylolpropane, trimethylolbutane, pentaerythritol and dipentaerythritol;
  lower alkyl-glucosides, especially those having from 1 to 8 carbon atoms in the alkyl radical, for example methyl and butyl glucoside;
  sugar alcohols having from 5 to 12 carbon atoms, for example sorbitol or mannitol;
  sugars having from 5 to 12 carbon atoms, for example glucose or saccharose;
  amino sugars, for example glucamine;
  dialcohol amines, such as diethanolamine or 2-amino-1,3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations. As insect-repellents, N,N-diethyl-m-toluamide, 1,2-pentanediol or insect-repellent 3535 are suitable examples.

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calamus), from wood (pinewood, sandalwood, guaiacum wood, cedarwood, rosewood), from herbs and grasses (tarragon, lemon grass, sage, thyme), from needles and twigs (spruce, pine, Scots pine. mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxy-ethyl isobutyrate, p-tert-butylcyclohexyl acetate, linalyl acetate, dimethyl-benzyl-carbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α,β-isomethylionone and methyl cedryl ketone; the alcohols include, for example, anethol, citronellol, eugenol, isoeugenol, geraniol, linalool, phenyl ethyl alcohol and terpineol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, cinnamon leaf oil, lime blossom oil, juniper berry oil, vetiver oil, olibanum oil, galbanum oil, labdanum oil and lavandin oil. Preference Is given to the use of bergamot oil, dihydromyrcenol, lilial, lyral, citronellol, phenyl ethyl alcohol, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, α-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane), diclosan, 4-(2-tertbutyl-5-methylphenoxy)phenol or TCC (3,4,4'-trichlorcarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil and also fractions from the steam extract of the wood and/or bark of Callitris intratropica, which is also known as "blue cypress oil". Glycerol monolaurate has also proved to be a bacteriostatic agent. The amount of the additional bacteria-inhibiting agents present is usually from 0.1 to 2% by weight, based on the solids content of the preparations.

It is furthermore possible for the cosmetic compositions to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, α-alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or β-mercaptoethanesulfonic acid, or oxidising agents, such as hydrogen peroxide, potassium bromate or sodium bromate.

Cosmetic formulations according to the invention are contained in a wide variety of cosmetic preparations. There come into consideration, for example, especially the following preparations:

preparations for treatment of the skin for the purpose of lightening, de-colouring or bleaching it;

preparations for the removal of freckles, age spots or melanin spots or skin marks or for treating hyperpigmentation;

skin-care preparations, e.g. skin-washing and cleansing preparations in the form of tablet-form or liquid soaps, synthetic detergents or washing pastes, skin-care preparations, e.g. body lotions, skin emulsions, multi-emulsions or skin oils;

cosmetic personal care preparations, e.g. facial make-up in the form of day creams or powder creams, face powder (loose or pressed), rouge or cream make-up, lipcare preparations, e.g. lipsticks, lip gloss, lip contour pencils, nail-care preparations, such as nail varnish, nail varnish removers, nail hardeners or cuticle removers;

special deodorants and antiperspirants or callus-removing preparations;

light-protective preparations, such as sun milks, lotions, creams or oils, sunblocks or tropicals, or after-sun preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams.

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a make-up, in the form of a stick, in the form of a spray (spray with propellent gas or pump-action spray) or an aerosol, in the form of a foam, or in the form of a paste.

Of special importance as cosmetic compositions for the skin are:

compositions for treatment of the skin for the purpose of lightening, de-colouring or bleaching it, for the removal of freckles, age spots or melanin spots or skin marks or for treating hyperpigmentation, such as skin milks, lotions, creams, oils, gels and sprays and also pastes light-protective compositions, such as sun milks, lotions, creams, oils, sunblocks or tropicals, after-sun preparations. Of particular interest are sun protection creams, sun protection lotions, sun protection oils, sun protection milk and sun protection preparations in the form of a spray.

The following Examples serve to illustrate the invention, without limiting it thereto.

EXAMPLES

Formulation Examples

Example 1

Face Cream Formulation

A face cream is prepared and contains the following constituents:
3.0% by weight glycerol monostearate,
1.5% by weight beeswax,
0.5% by weight sorbitan monooleate,
5.0% by weight liquid petrolatum,
10.0% by weight paraffin,
1.0% by weight lecithin,
0.5% by weight sodium N-stearoyl-L-glutamate,
0.15% by weight xanthan gum,
0.2% by weight (−)-guaiol,
0.1% by weight kojic acid,
0.1% by weight methylparaben, and
$H_2O$ ad 100% by weight.

Example 2

Skin Lotion Formulation 0.2% by weight (−)-guaiol,
0.2% by weight kojic acid,
0.2% by weight polyoxyethylene,
3.0% by weight compound of formula (3c),
1.0% by weight compound of formula (7),
0.05% by weight castor oil,
2% by weight 1,3-butylene glycol,
10% by weight ethanol,
perfume oils, stabilisers, and water to 100 parts by weight.

Example 3

Spray Formulation 0.1-0.5% by weight guaiol;
0.5-0.1% by weight kojic acid;
2.0% by weight of solubiliser LRI (from Lcw),
absolute ethanol 70% made up with water to 100 parts by weight.

Example 4

Oil-in-water Formulation:

0.05-0.5% by weight guaiol and another skin-lightening substance;
0.05-5% by weight one or more UV absorbers;
12% by weight glyceryl stearate;
6% by weight paraffin oil;
6% by weight caprylic/capric triglyceride;
4% by weight glycerol;
0.2% by weight disodium EDTA;
1.0% by weight citrate and
water to 100 parts by weight.

Application Examples

Example 5

In a test on 20 Asian test subjects
pure guaiol 0.2% and
guaiol in admixture with kojic acid (0.2%+0.1%)

are tested against the two commercial products well-known in China, "SRO-HC spray" and "Yue-sai/Coty Blanc natural whitening cream" (SRO-HC) (=benchmark).

The following compositions are used as the test formulation for the skin test:
2% by weight solubiliser LRI (from Lcw),
70% by weight absolute ethanol and
q.s. 100% deionised water.

Example 5a

Together With 0.2% (−)-guaiol;

Example 5b

Together with 0.2% (−)-guaiol and 0.1% kojic acid.

The results are shown in FIG. 1 wherein skin lightening is measured as a chance in L* or Delta L which is chart of the L, a, b color scale and is calculated using the CIE system from the reflectance values.

The results show that, after a treatment period of 12 weeks, better lightening action can be seen than in the case of the benchmark.

What is claimed is:

1. A method of inhibiting melanogenesis, which comprises contacting skin with an effective amount of a composition comprising
   (a) (−)-guaiol which originates from *Callitris intratropica* and
   (b) further skin-lightening active substance(s) selected from the group consisting of quercitin, aloesin, azelaic acid and esters thereof.

2. A method according to claim 1, wherein the ratio of component (a):(b) is from 1:99 to 99:1% by weight of component (b).

3. A method according to claim 1, wherein the composition additionally comprises, as component (c), one or more UV-A and/or UV-B absorbers.

4. A method according to claim 3, wherein as UV-A and/or UV-B absorber there is used a compound of formula

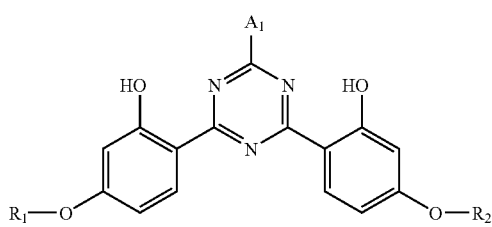

(2)

wherein
$R_1$ and $R_2$ are each independently of the other $C_3$-$C_{18}$alkyl; $C_2$-$C_{18}$alkenyl; a radical of formula —$CH_2$—CH(—OH)—$CH_2$—O—$T_1$; or $R_1$ and $R_2$ are a radical of formula

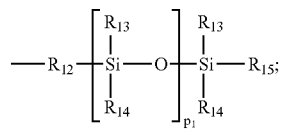

$R_{12}$ is a direct bond; a straight-chain or branched $C_1$-$C_4$alkylene radical or a radical of formula —$C_{m_1}H_{2m_1}$— or —$C_{m_1}H_{2m_1}$—O—;
$R_{13}$, $R_{14}$ and $R_{15}$ are independently of the others $C_1$-$C_{18}$alkyl; $C_1$-$C_{18}$alkoxy or a radical of formula

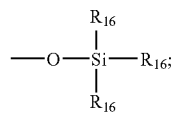

$R_{16}$ is $C_1$-$C_5$alkyl;
$m_1$ and $m_3$ are each independently of the other from 1 to 4;
$p_1$ is 0 or a number from 1 to 5;

$A_1$ is a radical of formula

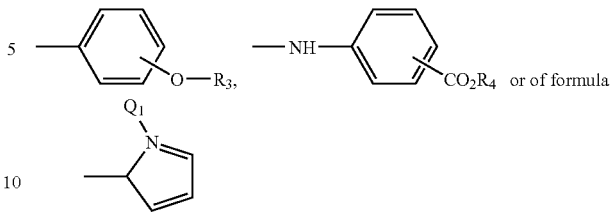

$R_3$ is hydrogen; $C_1$-$C_{10}$alkyl; —(CH$_2$CHR$_5$—O)$_{n_1}$—$R_4$; or a radical of formula —CH$_2$—CH(—OH)—CH$_2$—O—$T_1$;
$R_4$ is hydrogen; M; $C_1$-$C_5$alkyl; or a radical of formula —(CH$_2$)$_{m_2}$—O—$T_1$;
$R_5$ is hydrogen; or methyl;
$T_1$ is hydrogen; or $C_1$-$C_8$alkyl;
$Q_1$ is $C_1$-$C_{18}$alkyl;
M is a metal cation;
$m_2$ is from 1 to 4; and
$n_1$ is 1-16.

5. A method according to claim 4, wherein the composition comprises, as component (c), the compound of formula (3c)

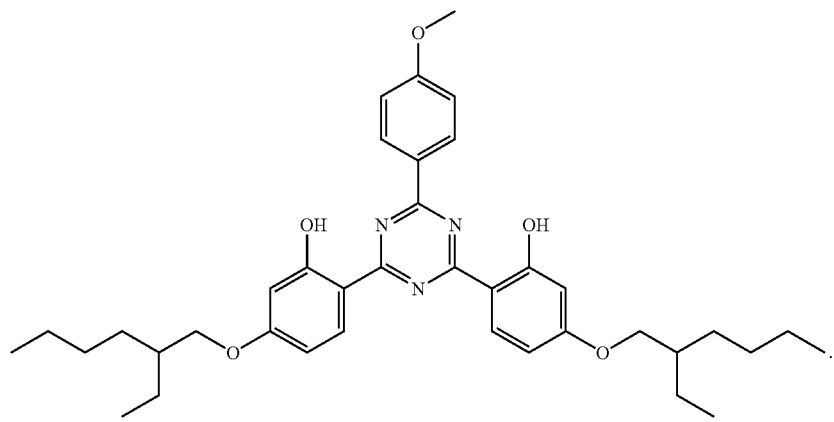

6. A method according to claim 1, wherein the composition comprises, as component (c), the compound of formula (7)

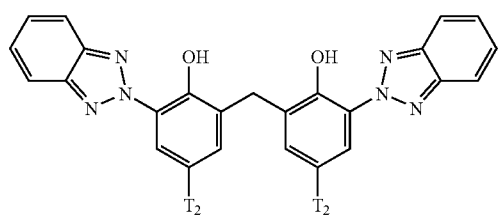

wherein $T_2$ is $C_1$-$C_{12}$alkyl.

7. A method according to claim 6, wherein $T_2$ is iso-octyl.

8. A method according to claim 1, wherein the composition comprises, as component (c), octyl methoxycinnamate.

9. A method according to claim 1, wherein the composition comprises, as component (c), benzophenone 3.

10. A method according to claim 1 whereby skin is lightened.

11. A method in which a composition according to claim 1 is incorporated into a cosmetic formulation.

12. A method according to claim 11, wherein the composition is in the form of an oil-in-water formulation, in a solvent formulation or in the form of a paste formulation.

13. A method according to claim 11, wherein the amount of the composition in the formulation is from 0.01% to 10% by weight.

14. A cosmetic formulation according to claim 11 comprising (a) (−)-guaiol, (b) further skin-lightening active substance(s) and, optionally, (c) one or more UV-A and/or UV-B absorbers.

15. A cosmetic formulation according to claim 14, comprising (a) from 0.01 to 5% by weight of (−)-guaiol, (b) from 0.01 to 5% by weight of further skin-lightening active substance(s) and, optionally, (c) from 0 to 30% by weight of one or more UV-A and/or UV-B absorbers.

* * * * *